(12) United States Patent
Payumo et al.

(10) Patent No.: US 7,875,290 B2
(45) Date of Patent: Jan. 25, 2011

(54) METHOD AND FORM OF A DRUG DELIVERY DEVICE, SUCH AS ENCAPSULATING A TOXIC CORE WITHIN A NON-TOXIC REGION IN AN ORAL DOSAGE FORM

(75) Inventors: Francis C. Payumo, Somerville, MA (US); Jill K. Sherwood, Edison, NJ (US); Donald C. Monkhouse, Radnor, PA (US); Jaedeok Yoo, West Orange, NJ (US); Christopher M. Gaylo, Princeton Junction, NJ (US); Chen-Chao Wang, West Windsor, NJ (US); Michael J. Cima, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 223 days.

(21) Appl. No.: 11/246,910

(22) Filed: Oct. 7, 2005

(65) Prior Publication Data

US 2006/0110443 A1    May 25, 2006

Related U.S. Application Data

(63) Continuation of application No. 09/861,480, filed on May 18, 2001, now Pat. No. 7,276,252.

(60) Provisional application No. 60/205,896, filed on May 18, 2000.

(51) Int. Cl.
*A61K 31/4745* (2006.01)
*A61K 31/198* (2006.01)
*A61K 9/48* (2006.01)

(52) U.S. Cl. .................. 424/451; 514/283; 514/567

(58) Field of Classification Search ................. 424/451; 514/283, 567
See application file for complete search history.

(56) References Cited

U.S. PATENT DOCUMENTS 2,801,203 A    7/1957    Leb et al. ................ 424/9.411

(Continued)

FOREIGN PATENT DOCUMENTS

EP    0 659 432 A1    6/1995

(Continued)

OTHER PUBLICATIONS

Burke and Bom, "Campthothecin Design and Delivery Approaches . . . ," *Annals of the New York Academy of Sciences* 922: 36-45, 2000.

(Continued)

*Primary Examiner*—Robert A Wax
*Assistant Examiner*—Aradhana Sasan
(74) *Attorney, Agent, or Firm*—Rick Matos; Innovar, L.L.C.

(57) ABSTRACT

A drug delivery device such as an oral dosage form (ODF) with a toxic or potent core encapsulated by a non-toxic region. The non-toxic region may be a region including multiple layers, coatings, shells, and combinations thereof, which provides protection to and isolation from the toxic or potent core. The drug in the toxic or potent core is incorporated into the dosage form via, for example, three-dimensional printing, as a solution, solubilization or suspension of solid particles in liquid, rather than by the more conventional handling and compressing of dry powder. This minimizes the likelihood of creating airborne particles of the toxic drug during manufacturing, hence controlling and minimizing the exposure of manufacturing personnel to the hazardous substance. Wet dispensing of the toxic or potent drug further provides greater bioavailability of the drug to the patient.

27 Claims, 6 Drawing Sheets

U.S. PATENT DOCUMENTS

| | | | |
|---|---|---|---|
| 4,943,579 A * | 7/1990 | Vishnuvajjala et al. | 514/283 |
| 5,082,669 A | 1/1992 | Shirai et al. | 424/495 |
| 5,215,989 A | 6/1993 | Baldwin et al. | 514/252 |
| 5,314,696 A | 5/1994 | Paulos | 424/453 |
| 5,597,829 A * | 1/1997 | Hausheer et al. | 514/283 |
| 5,783,212 A | 7/1998 | Fassihi et al. | 424/472 |
| 6,046,177 A | 4/2000 | Stella et al. | 514/58 |
| 6,294,199 B1 | 9/2001 | Conley et al. | 424/468 |
| 6,506,407 B2 | 1/2003 | Watanabe et al. | 424/463 |
| 6,514,518 B2 * | 2/2003 | Monkhouse et al. | 424/427 |

FOREIGN PATENT DOCUMENTS

| | | |
|---|---|---|
| EP | 0 671 167 A1 | 9/1995 |
| WO | WO 94/09762 | 5/1994 |
| WO | WO 98/36739 | 8/1998 |

OTHER PUBLICATIONS

Physician's Desk Reference, "Procardia" (printout), Dec. 9, 2001, pp. 1-12.

* cited by examiner

Capsule design

Tablet Design

METHOD AND FORM OF A DRUG DELIVERY DEVICE, SUCH AS ENCAPSULATING A TOXIC CORE WITHIN A NON-TOXIC REGION IN AN ORAL DOSAGE FORM

CROSS-REFERENCES TO RELATED APPLICATIONS

This application is a continuation of U.S. patent application Ser. No. 09/861,480 filed May 18, 2001 (now U.S. Pat. No. 7,276,252), which application claims the benefit of U.S. Provisional Patent Application No. 60/205,896 filed May 18, 2000. Both of these applications are incorporated herein by reference in their entireties.

TECHNICAL FIELD

This invention relates generally to pharmaceutical delivery systems and more particularly to an oral dosage form including a non-toxic region encapsulating or surrounding a pharmaceutically toxic or potent core.

BACKGROUND OF THE INVENTION

Oral dosage forms (ODFs) of drugs have previously been surrounded by a coating that had properties different from the properties of the interior. For example, coated tablets were the subject of U.S. Pat. No. 5,914,132, within which the coating allowed delivery of the drug to the colon, with its particular chemical environment, rather than in an earlier part of the gastrointestinal tract with its different chemical environment, such as pH and enzymatic system.

Methods and apparatus for coating pharmaceuticals were disclosed in U.S. Pat. No. 4,497,847, which disclosed methods for applying the coating to the pharmaceutical via spraying or immersing in a centrifugal fluidized coating apparatus or a fluidized bed granulating coating apparatus. These coatings were intended to provide various controlled-release profiles. Most commonly the main interior part of the tablet was formed by compression of powder.

In these and similar patents, the drug was not especially toxic or hazardous, and the coating did not serve the purpose of isolating the toxic or hazardous substance from personnel who manufacture or handle the product. Therefore, no unusual handling or manufacturing precautions beyond those ordinarily employed in the pharmaceutical industry were necessitated due to the properties of the drug. Furthermore, the coating process was usually performed on finished tablets or pellets that had been manufactured by a separate process, and not concurrent with the manufacture of the pharmaceutical form. Therefore, the coating process itself did not circumvent the powder-mixing step during manufacture, in which airborne particulate matters could be generated. Airborne particulate matters of highly toxic or potent pharmaceuticals created problems for manufacturing personnel and non-patient personnel that required special handling procedures. These procedures have often been both ineffective and expensive.

Soft gelatin capsules have been used to deliver actives in dissolved, solubilized, or suspended forms. Soft gelatin capsules have the advantages of avoiding exposure to airborne hazardous particles as well as achieving better content uniformity than other solid dosage forms. However, migration of solute and the actives from the liquid phase to the gelatin shell have been a major drawback. Soft gelatin capsules were also not suitable for formulation of actives which require long release duration, since the capsule itself did not sustain drug release. Soft gelatin capsules have therefore not been used with a drug that was highly toxic, potent or otherwise hazardous.

Some pharmaceuticals, such as anti-cancer drugs, are highly toxic. For example, 9-nitrocamptothecin is used to treat pancreatic cancer, and yet is so toxic that companies are unwilling to manufacture it into solid dosage forms because of the exposure danger inherent in conventional manufacturing techniques. There are also other types of pharmaceutical actives, such as hormones, that are so potent that non-patient personnel must not be exposed to even small quantities of them. Thus, there is a need for manufacturing techniques and ODFs which are better suited to the handling, both during and after manufacture, of substances which are highly toxic or potent or otherwise hazardous to non-patients.

One attempt to address handling issues of toxic components during manufacturing of ODFs was disclosed in WO 94/09762. The active ingredient was in liquid form and was applied to the core of the ODF as a film coating, and which was optionally surrounded by an overcoating for further isolation. This manufacturing technique involved a substantial number of sequential manufacturing steps and could only incorporate the amount of drug that was contained in the one thin layer that the liquid coating formed around the central form. Drugs that had low solubility were thus precluded.

Three dimensional printing (3DP) techniques have been used to manufacture medical devices as disclosed in U.S. Pat. Nos. 5,490,962; 5,869,170; and 5,518,680. However, 3DP manufacturing of medical devices failed to overcome many of the post processing steps, such as applying a coating, that were found in conventional manufacturing. Additionally, 3DP manufacturing of medical devices required a final step of removing and dedusting the medical device from the loose unbound powder in the powder bed. Dedusting removed some powder particles at the surface of the medical device that were not securely bound to the main body of the product. Dedusting included agitation applied to the medical device to remove loose powder particles and partially bound particles. When manufacturing a medical device with a hazardous material, loose powder particles can be problematic to the manufacturer. Furthermore, varying dedusting techniques may result in variations in drug quantity.

SUMMARY OF THE INVENTION

The present invention overcomes the limitations of the prior art and provides additional benefits. Under one aspect of the present invention, a pharmaceutical delivery system such as an oral dosage form (ODF) includes a hazardous drug encapsulated by a non-toxic region. This non-toxic region may be a pharmacologically inert substance and is a region such as a layer, a coating, or a shell that provides an isolation barrier between the toxic or potent interior and exterior contact.

Another aspect of the present invention includes a manufacturing technique by which the toxic drug is incorporated into the individual ODF as a solution, aqueous suspension, or by solubilization, rather than by the more conventional compression of powder. This minimizes the likelihood of creating airborne particles of the toxic drug during manufacturing, hence controlling and minimizing the exposure of manufacturing personnel to the toxic compounds. Incorporating the drug as a solution, solubilization or aqueous suspension further allows greater bioavailability of the drug to the patient.

DETAILED DESCRIPTION OF THE INVENTION

A drug delivery device, and in particular, a method for manufacturing a pharmaceutical in the form of an oral dosage form (ODF) with a toxic or potent drug encapsulated by a non-toxic region wherein the non-toxic region may be a pharmacologically inert substance. The non-toxic region provides an isolation barrier or buffer zone protecting the toxic or potent core from damage during handling or from early release of the drug. The non-toxic substance is fabricated to encapsulate the core with a region that includes an unbound region of powder, a layer of non-toxic drug, a coating, a shell, or any combination thereof. The toxic drug may be incorporated into the delivery device as a solution, suspension, or by solubilization, which serves to minimize toxic airborne particles while providing greater bioavailability of the drug to the patient. In the following description, numerous specific details are provided, such as a manufacturing technique by which the toxic drug is put into the individual ODFs as a solution, suspension, or by solubilization, rather than by handling loose powder. One skilled in the relevant art, however, will recognize that the invention can be practiced without one or more of the specific details, or with other actives or inert substances. In other instances, well-known structures, operations or processes are not shown or not described in detail to avoid obscuring aspects of the invention.

One manufacturing technique suitable for making the dosage form of the present invention is of the family known as Solid Free-form Fabrication (SFF). SFF involves building up arbitrary shapes from powder, for example, with Three Dimensional Printing or with Selective Laser Sintering, or from a liquid or paste, for example, with Stereolithography. One SFF process is Three-Dimensional Printing (3DP) described in U.S. Pat. No. 5,204,055 issued to Emanuel Sachs et al.

As illustrated in FIG. 1, a 3DP apparatus includes a printer 100 including a first axis 110 of movement, a second axis 120 of movement which may be perpendicular to the first axis of movement 110, and a liquid dispensing device 130. The dispensing device 130 can dispense drops 140 of a first liquid onto a powder bed 150. The layer of powder 150 is laid down, by a roller or other method such as slurry deposition. Liquid is dispensed onto predetermined regions of the powder bed by the dispensing device 130 for dispensing small quantities of liquid drops 140, typically resembling an ink-jet printhead. For example, it could be a microvalve (Lee Company, Essex, Conn.) or it could be a piezoelectric drop-on-demand printhead as is know in the art. This causes particles of the powder bed 150 in the wetted regions to fuse or bind together, either by dissolution and resolidification or by the adhesive action of the liquid drops 140. Sometimes a powdered binder is included in the powder bed 150 and when it is exposed to liquid drops 140 it binds other particles. After this liquid dispensing process is completed on one layer, another layer of powder is spread and the liquid dispensing is repeated, and so on until a complete three-dimensional object has been built.

During printing, the unbound powder supports the bound shape and the later deposited layers of powder. At the end of the printing process the unbound and untrapped powder is removed, leaving only the shape which has been bound together. At each powder layer, timing of drop ejection is coordinated, for example by software, with the motion of the printhead in two axes 110, 120, to produce almost any desired shape of bound product potentially including details of great complexity.

For applications such as the present one, it may be further desirable to include a second dispenser 132 for dispensing drops 142 of a second liquid. The second dispenser 132 is shown as being mounted on the same motion system and printhead as the first dispenser 130. Alternatively, the second dispenser 132 could be mounted on a separate motion system. If the second dispenser 132 is separately mounted, it may be preferable to provide a system of suitable registration or coordination locating the two dispensers 130, 132, so that each dispenser can deposit liquid in a predetermined location accurately relative to the location of liquid deposited by the other dispenser.

The present invention is directed toward pharmaceutical dosage forms, for example, oral dosage forms (ODFs). ODFs typically include a bulk material, a binder and an active agent. The powder or bulk material may be composed of typical pharmaceutical excipients such as are known in the art. Examples of excipients include but are not limited to microcrystalline cellulose, lactose, mannitol and dicalcium phosphate.

Binder is dispensed onto the bulk material. Binder may be a liquid, a powder or some combination of a liquid and a powder referred herein as a slurry or a suspension. Binder may further be a liquid containing solubilized active. By solubilization, compounds that are typically insoluble can form micelles to increase the solubility in the dispersing system when surfactant or solubilizer is added to the system. Surfactants form aggregates of molecules or ions called micelles when the concentration of the surfactant solute in the bulk of the solution exceeds a limiting value, the so-called critical micelle concentration (CMC). The formation of micelles is referred to herein as a solubilization process.

One possible purpose of the binder is to carry the drug or active agent to the delivery system. Another possible purpose is to cause particles to bind to each other, in which case it is referred to herein as a binding agent. The binder may further serve both of these functions or some portion thereof. Binding of the particles can occur through several mechanisms. One mechanism is that the binder is a liquid that acts as a solvent of the bulk material or powder, in which case the liquid actually dissolves powder particles. As the solvent in the liquid evaporates, the particles resolidify such that they are joined together. Another mechanism is that the liquid binder simply solidifies around solid particles thereby binding them. Yet another mechanism is that the liquid binder may contain a dissolved adhesive substance that is left behind when the liquid evaporates to bind the particles together. The dissolved substance may be a plasticizer, for example, a polymeric material, which modifies the chemistry of the bulk material to cause bonding. Plasticizers are incorporated into a polymer to increase its workability, flexibility, or distensibiltiy by increasing the free volume between the polymer molecules. The increase in free volume will increase the freedom of movement for polymer molecules and therefore provide better fusing between polymer particles. Plasticizers are usually moderately high molecular weight liquids, or occasionally, low melting solids. Examples of commonly used plasticizers include, but are not limited to, carboxylic acid and phosphoric acid esters. Yet another mechanism for binding includes the powder bulk material containing particles of a binder in solid form that are activated upon absorption of certain solvents.

Figure 1:
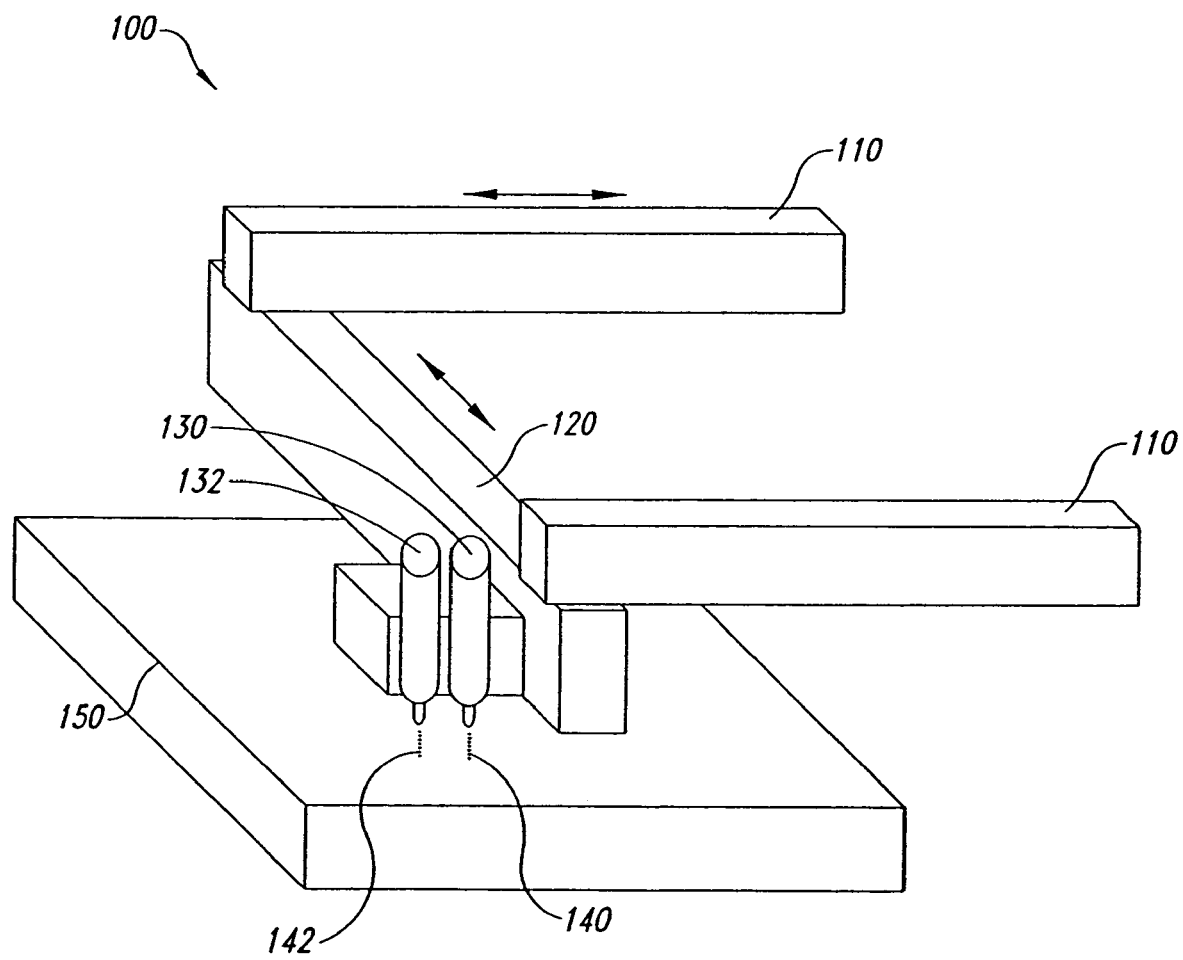
FIG. 1 is an isometric view of a three dimensional printing apparatus in accordance with one embodiment of the invention.

In the present application, the active agent or drug is deposited in a central region or core of the dosage form. A liquid containing toxic or potent drug is herein referred to as the core binder. This is shown in FIG. 1 as a liquid drop 140 containing a pharmaceutical active being dispensed to place a drug or a combination of drugs in specified regions of the powder bed 150. The core binder preferably functions as a binding agent, thus causing powder particles to adhere together, but it is not essential that it function as a binding agent. The liquid may simply serve as a means of placing the drug within the dosage form.

In accordance with one embodiment of the present application, there is a second liquid 142 concurrently dispensed to form an encapsulated region around the region containing the active. The second liquid 142 serves as a binding agent to bind the powder or bulk material and creates the region encapsulating the hazardous core. This second liquid is herein referred to as the shell binder. The shell binder does not contain a toxic or potent drug although it may contain an active drug with other therapeutic purposes.

The shell binder may include a non-toxic active that is complementary to the toxic drug in the core region, a pretreatment to the drug in the core, or even counteractive to a feature of the drug in the core. For example, an anti-cancer drug in the core could be paired with an anti-emetic or anti-vomiting drug placed in the shell binder. Other examples of additives or actives that may be incorporated in the shell binder include taste-masking actives, sugar, additives to increase the physical integrity and reduce friability of the dosage form, or additives to delay the release of the core drug based on pH of environment or based on duration of ingestion.

Figure 2:
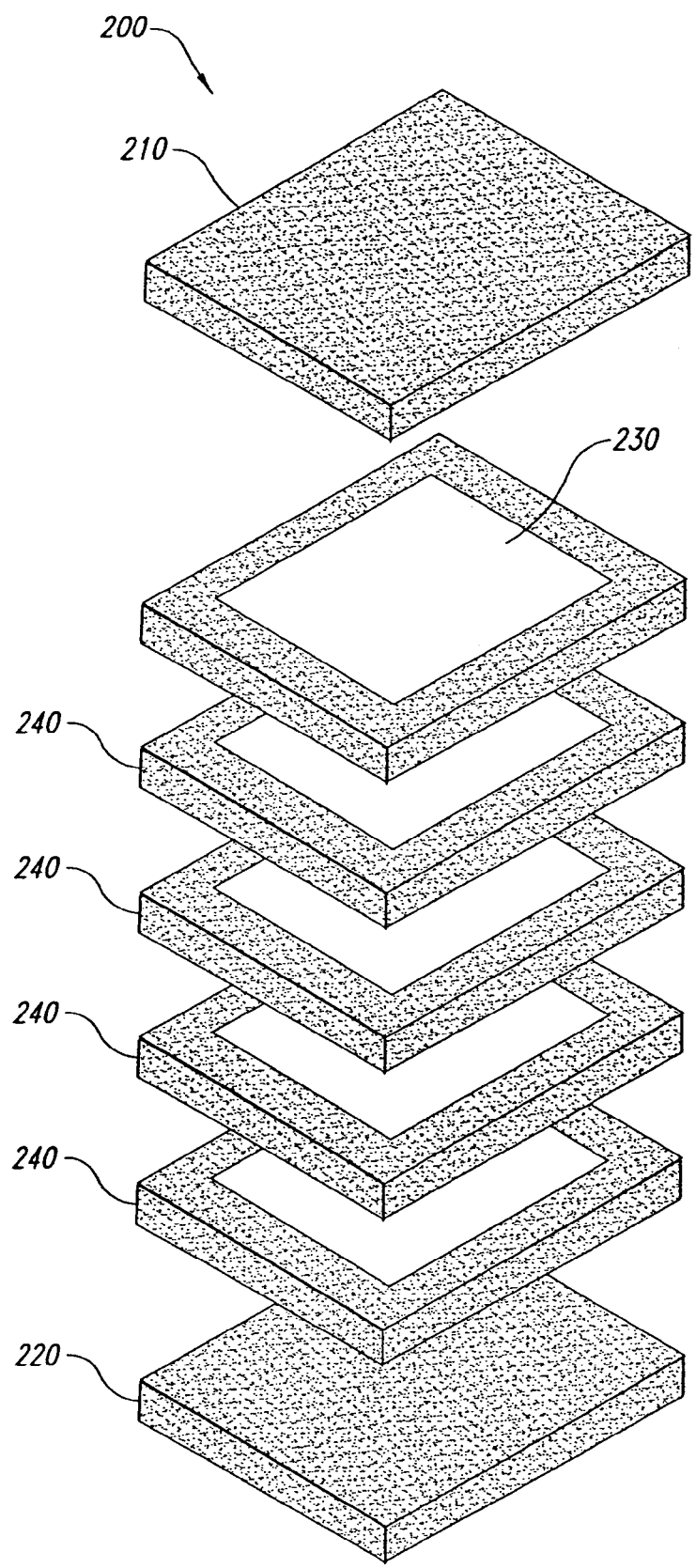
FIG. 2 is an exploded isometric view of a pharmaceutical form in accordance with one embodiment of the invention.
Figure 3:
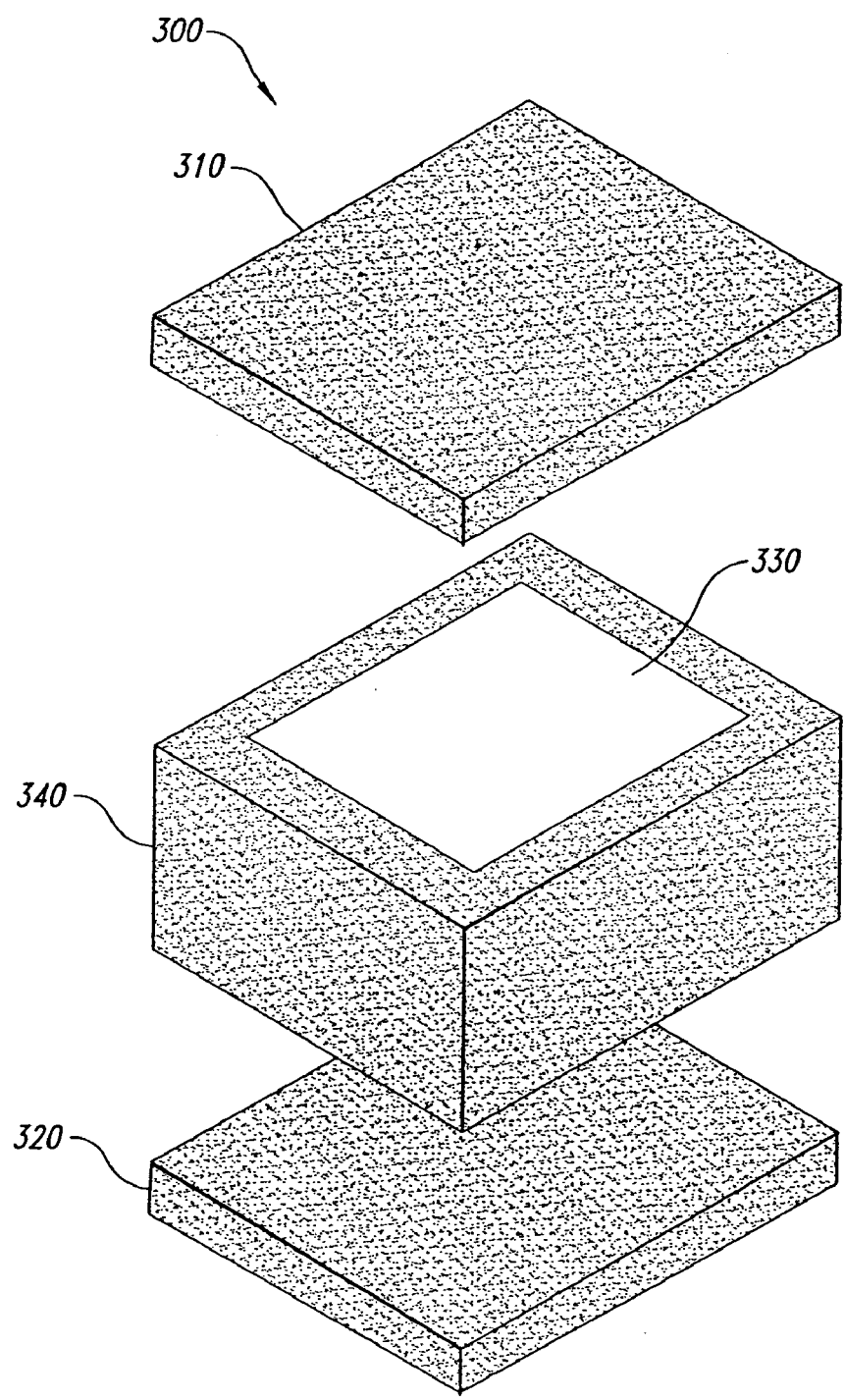
FIG. 3 is a partially exploded isometric view of the pharmaceutical form of FIG. 2 in accordance with one embodiment of the invention.

FIGS. 2 and 3 illustrate ODFs 200 and 300 in which a box or shell encloses the active core. In FIG. 2, individual layers of the ODF 200 are exploded apart for clarity of illustration. A top 210, a bottom 220 and walls 240 surround core 230, which contains a toxic or potent drug. In any individual layer where drug is deposited, a non-toxic region 240 forms a closed curve around the region in which drug has been deposited. This non-toxic region can be a pharmaceutically inert substance or a region containing therapeutic but non-toxic drugs. Top and bottom 210 and 220 also form non-toxic regions. Considering all three dimensions, all of the non-toxic closed curves or regions on individual layers taken together form a non-toxic enclosing surface region or shell. This non-toxic region acts as a boundary or isolation region between the toxic core and the handlers and may include multiple regions including transition regions, layers, coatings, shells, or combinations thereof.

FIG. 3 illustrates an ODF similar to FIG. 2, but with simpler construction. The top of the box 310 and the bottom of the box 320 are shown in an exploded view. In this embodiment, the walls are constructed as a thickened layer. In this figure the active hazardous core 330 is shown surrounded by the top 310, the bottom 320 and walls 340.

One exemplary method of manufacturing the dosage form in accordance with the present invention is by building one or more bottom layers with a drug-free or non-toxic binder in the shape of the intended geometry of the dosage form. Subsequent layers would include concurrently or sequentially dispensed toxic core drug placed within the footprint of the bottom layers and drug-free or non-toxic binder fluid placed around an encapsulating perimeter of the toxic core.

The walls 240, 340 are formed by binding together portions of powder, again using the non-toxic shell binder, to define a closed region on the sides, including all areas surrounding the toxic core which are not already bounded by the bottom or top. The walls 240, 340, as well as the top and bottom 210, 310, 220, 320, may be referred to as the shell, and the binder which binds the walls 240, 340 and top 210, 310 and bottom 220, 320 may be referred to as the shell binder.

In one embodiment, powder in an intermediate or transition region between the shell and the core is not bound together but is trapped in place between the core and the shell. Alternatively, the transition region 230, 330 shown as the walls 240, 340 of the dosage form in FIGS. 3 and 4 may include multiple regions of bound and unbound powder including non-toxic pharmaceutical excipients or other inert substances.

The walls 240, 340 at each layer are further bound to the bound region of the layer below it and the layer above it, thus encapsulating the toxic core. The layers above and below may be layers in which the shape of the shell boundary is printed or may be the top or bottom. A top for the box may be created in much the same way as the bottom.

The illustrated embodiment produces an enclosure that is a hollow rectangular parallelepiped. However, it should be recognized that any other shape, for example, a cylinder, ellipsoid, rod, or sphere, could also be produced. Any of these shapes could further be placed, either singly or in a group, inside a capsule.

Pharmaceuticals incorporating a powder are characterized by friability, namely, the tendency for particles of the surface to rub off or break off from attrition during processing or handling. Friability is a measure of fragility. In the present invention, if such breaking off of particles does occur, such particles are the non-toxic exterior surface of the dosage form. This represents a significant advantage over the prior art. However, it is still desirable that the completed device not be excessively friable. If the device were extremely friable, the particles may break off to expose the toxic core. The friability will be determined by the composition of the shell. Accordingly, the composition of the shell, namely the powder and shell binder, should be selected so that the finished product has at least a moderate amount of resistance to chipping, breakage, attrition, friction, and the like. Material selections for achieving this are known in the art and are further described in the Examples.

The core binder and optionally the shell binder may contain a pharmaceutical active as a dissolved solute. Alternatively, either of these binders may be a suspension containing solid particles of the drug suspended in the liquid, if for example, the drug is not sufficiently soluble in the liquid being used. In yet another embodiment, the binder may contain an active in solubilized form.

Wet dispensing of the toxic or potent drug in a solution, microfine suspension, or in solubilized form allows a solid dosage form to include a toxic or potent drug in an amorphous state. Providing a drug in an amorphous state is advantageous because it results in a drug with higher bioavailability to the patient than a drug that is allowed to exist in a crystalline form. Drugs in an amorphous, non-crystalline state are better absorbed by the body than drugs in a crystalline state due to the higher surface area for dissolution and absorption.

Yet another advantage of the present invention is that when the drug is in amorphous form with the presence of crystallization inhibitors, crystal growth can be inhibited, thus enhancing the absorption of the drug. Steric hindrants, such as PVPs, HPMCs, or surfactants in a binder solution that contains the active will inhibit the recrystallization of the active in the dosage form after drying. Therefore, the resolidified active particles will either be in amorphous form or have very small crystal size. As a result, the absorption will be enhanced as compared to the original solid state of the active because the increase in surface area for the dissolution and hence absorption will enhance the bioavailability of the drug.

Another factor relevant to achieving isolation of the toxic core relates to bleeding. Bleeding is the spreading of liquid in the powder bed after the liquid is printed but before it dries. Bleeding occurs by capillary action, and is a common concern in 3DP because it affects dimensional accuracy and surface finish. Bleeding can occur in the horizontal direction in a powder layer and in the vertical direction into previous or subsequent layers of powder. Bleeding in the vertical direction is less of a concern and as stated previously, will serve to bind subsequent layers together. Typically in 3DP, all of the printed regions on a layer are at least somewhat wet simultaneously. This contributes to the time efficiency of the process and to better interlayer adhesion between printed regions on adjacent layers. However, bleeding becomes a concern if it draws the toxic or potent pharmaceutical active closer to the surface than might be expected, resulting in poorer isolation than designed. For example, if the core and shell regions are printed approximately simultaneously and touch each other, the liquid in the two wet regions may intermix. This would result in the spread of the toxic or potent active beyond the geometric location where it was intended to be positioned.

One method of counteracting bleeding is to include a transition region in the dosage form. Therefore the toxic or potent active can spread without causing a problem or without actually reaching the shell binder. The transition region can be an encapsulating region around the toxic core that contains unbound powder, partially bound powder or bound powder.

Figure 4:
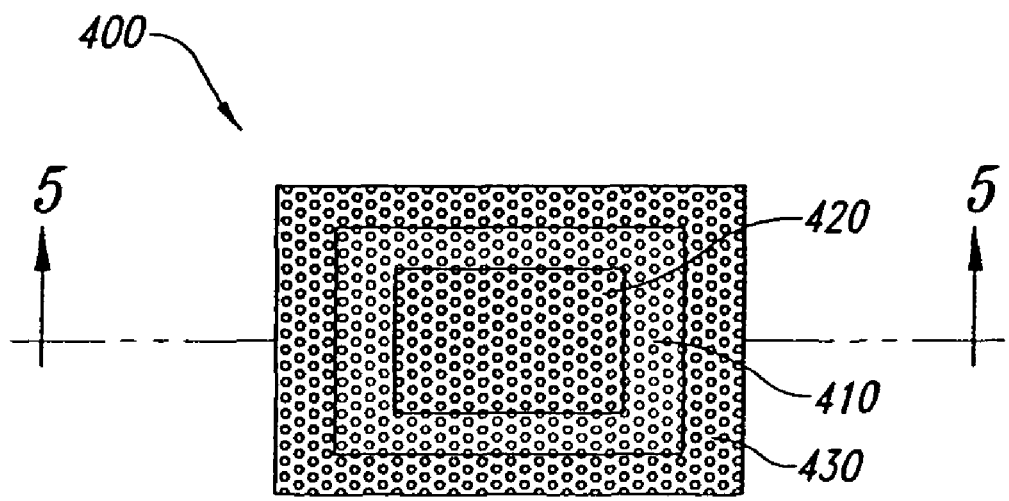
FIG. 4 is a section view of a pharmaceutical form illustrating a buffer region within an individual printed layer in accordance with one embodiment of the invention.

FIG. 4 illustrates one embodiment of the present invention in which the pharmaceutical form 400 includes a transition region 410. The transition region 410 is created between the drug-containing core 420 and the shell region 430 to absorb the possible bleeding or infiltration of the drug-containing liquid beyond the core region 420 where the drug-containing drops were actually placed. The transition region 410 thus prevents the toxic or potent drug from reaching or infiltrating into the shell. This is further illustrated in Example 1.

The transition region 410 can be constructed from unbound powder. In such a situation the toxic or potent core 420 would be innermost, the walls 430 of the box would be outermost, and between them would be a thin buffer region 410 which is not bound together and also does not contain a toxic or potent drug like the innermost region. If bleeding of the toxic or potent drug occurs, such bleeding could spread into the buffer or transition region 410 but would not actually reach the wall or shell 430.

Figure 5:
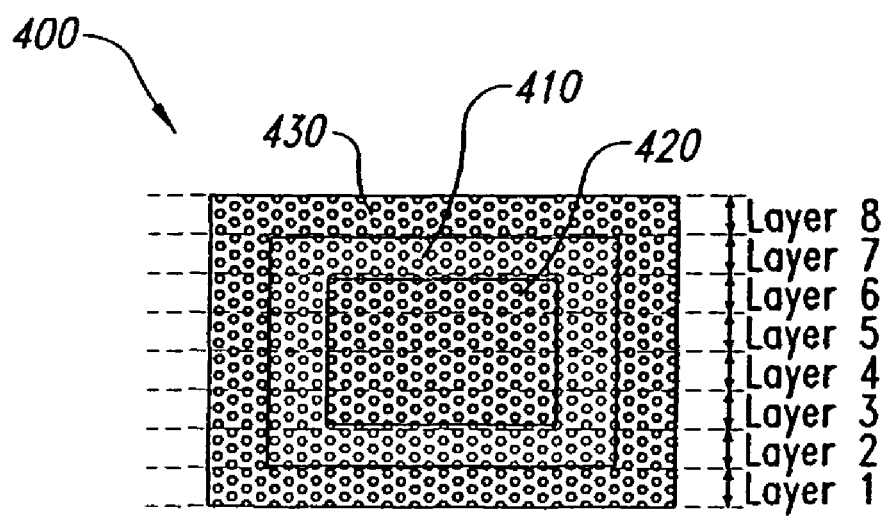
FIG. 5 is an elevation view of the pharmaceutical form of FIG. 4 along line 5-5 further illustrating the buffer region above and below the core region.

As shown in FIG. 5, one or more layers of powder above the bottom layer and one or more layers of powder just below the top layer allows the encapsulation of the toxic core 420 by the transition region 410. No core binder would be printed into these layers. This would provide opportunity to absorb possible bleeding in the vertical direction. This further helps achieve isolation of the drug or the hazardous core 420 from the outside world.

Another method of controlling bleeding is to appropriately select the excipients making up the powder. There are substances that may be included in the powder that form a gel when they absorb the binder liquid. Since the binder liquid is absorbed and immobilized, the gel will function as an infiltration barrier, with the result that the binder liquid does not spread further after it has interacted with this substance. An example of such a substance is hydroxypropylmethylcellulose (HPMC). Other examples for use with aqueous binder solution include polyvinyl alcohols (PVAs), polyethylene glycols, polyethylene oxides, carbopols, hydrophilic silica gel, xanthan gum, gellan gum, locust bean gum, acrylic acid polymers, gelatin, sodium carboxymethyl cellulose, methylcellulose, guar gum, sodium alginate, polyethylene-polypropylene copolymer, corn starch, and polyvinyl pyrrolidones (PVPs) and other hydrophilic polymers. Other examples for use with ethanolic binder systems include polyethylene glycols, polyethylene-polypropylene copolymers, polyoxyethylene alkyl ethers, polyvinyl pyrrolidones, and the like.

In conventional manufacturing of pharmaceuticals, it is the powder-handling steps which offer relatively great likelihood of dispersing quantities of substances where they are not wanted. Powders can be difficult to contain because powders include a range of particles sizes and the fine particles can become easily airborne. One advantage of the present invention, wherein the toxic or potent drugs are wet dispensed, is that the powder which is spread to form each layer can be composed of pharmacologically inert excipients, and so any particulates that might be dispersed from it are benign. In the present invention, the toxic or potent drugs are contained in the liquid that is dispensed. The hazardous substance can be liquid-dispensed even if it is non-soluble or only slightly soluble in the liquid, because if necessary the substance can be contained in the liquid as a suspension of solid particles, or in solubilized form. By virtue of this, it is possible to avoid the tendency found in tablet pressing techniques for particles of dry powder, containing drug to become airborne, which in the case of highly toxic or potent substance can present an exposure hazard to manufacturing personnel.

An additional advantage over the prior art is that the present invention provides encasement of toxic or potent drugs without contact of the toxic or potent drugs by either personnel or tooling. Furthermore, the dosage forms themselves do not bump into or touch each other during manufacturing. Non-contact of the dosage forms during manufacturing makes both the product and the process an improvement over previous techniques.

The finished form of the present invention is a solid which effectively immobilizes the toxic or potent pharmaceutical active that is in the core region with the encapsulating intermediate or transition region. This is a more complete immobilization than would be the case for an alternative packaging of a soft gel capsule, where liquid is surrounded by a gelatin shell. In a soft gel capsule there still can be a finite rate of diffusion of substances from the interior liquid into the surrounding capsule body.

This has the further advantage that when a 3DP dosage form is dedusted as described earlier, the possible dislodging of partially adhered particles from the surface of the dosage form does not remove any toxic drug, and hence dedusting cannot introduce any errors in the dosage of drug contained in individual dosage forms. This eliminates a possible randomizing influence on the final content of drug in the dosage form.

FIGS. 7A-7E illustrate a further embodiment of the present invention illustrating a dosage form that will release in two doses. This embodiment can be used to include two doses of an active in one single unit dosage form to enhance patient compliance and reliability. The first dose included in the shell region 730 can be immediately released upon administration. The transition region 720 between the shell region and the core region 710 can be fabricated with a high saturation level to generate a lag time. An example of this design is to include an anti-cancer compound and an anti-emetic compound in a single dosage form. Thus, the anti-emetic contained in the shell region 730 can have sufficient time to take effect before treatments resulting in nausea such as an anti-cancer treatment are administered. In this case the transition region 720 would be bound through the use of a binder which is a binding agent and which forms a time-delay region. This might be a third binder beyond the two already disclosed. Alternatively, for such a dosage form the design could be as follows, starting from the outside and progressing inward: a shell region containing an anti-emetic; an interiorly-located shell which is a time delay; a transition region which could be unbound powder for bleeding control; and a core region containing the toxic or potent drug; with all regions encapsulating the region immediately adjacent and interior to them.

The following examples are further provided for illustrative purposes.

Example 1

Drugs of particular interest are camptothecin (C20 H15 N3 O6) and its derivative, 9-nitrocamptothecin (9-NC) (rubitecan), and also other derivatives of camptothecin. These drugs are effective against pancreatic cancer, which is a particularly virulent form of cancer. 9-NC has an oral LD-50 (for mice) of 55 mg/kg acute, 2.5 mg/kg chronic. It is considered extremely dangerous to handle. In fact, its toxicity is part of what makes it useful against cancer. Despite the drugs' known effectiveness, drug manufacturers and packagers are reluctant to manufacture solid ODFs using the drug because of its toxicity and potential hazard to manufacturing personnel. If a conventional uncoated tablet of this pharmaceutical were made by tablet-pressing methods, airborne particulates would be a significant hazard to manufacturing and packaging personnel, and direct contact with the tablets would be a hazard to nurses, pharmacists, and other healthcare personnel. Because of this, the drug is relatively unavailable to patients, even though they have little other available treatment.

The oral dosage form in the present example was made using the 3DP process. The liquid used in dispensing this drug was an aqueous suspension. The drugs are essentially insoluble in water. Microfine camptothecin or 9-NC was incorporated into the suspension at a concentration of 2.5% (by weight). The average particle size was approximately 0.5 microns. Other substances included in the suspension were Avicel RC-591 (10% Na CMC, 90% microcrystalline cellulose) and PVP K-25 (polyvinyl pyrrolidone of a molecular weight of 25,000 g/mole), which function as a suspending agent and steric hindrant to prevent agglomerate formation, respectively. Drops were dispensed by electronically actuated microvalves made by the Lee Corporation, Essex Conn., through nozzles which were holes drilled through jewels as are commercially available from the Swiss Jewel Company, Philadelphia Pa. Dispensing by other methods, as are known in the art, could also be used.

The powder which was used to make the ODF matrix (the powder upon which printing was performed) was a mixture containing hydroxypropylmethyl cellulose (HPMC) and other excipients, such as Avicel CL-611, Avicel PH-301 and lactose. Avicel is manufactured by the FMC Corp., Philadelphia, Pa. Avicel CL-611 contains 85% of microcrystalline cellulose and 15% of sodium carboxymethyl cellulose (Na CMC). Na CMC functions as a solid binder that gels upon hydration. Avicel PH-301 is a type of microcrystalline cellulose, a water-insoluble excipient. HPMC is a gelation agent as already described. The quantity of HPMC can be varied to adjust the drug release rate. Addition of more HPMC effectively decreases the drug release rate. Flow rates of drug suspensions were adjusted to deliver a nominal total drug loading of 0.5 mg active to the core region of the ODF.

Figure 6A:
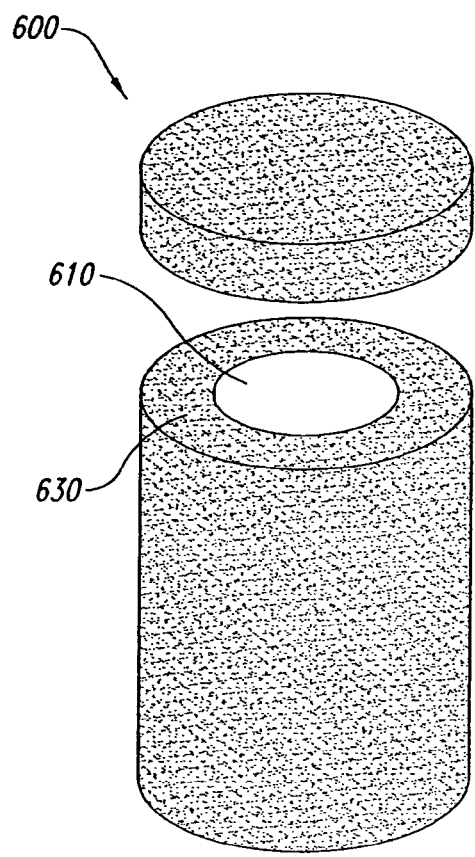
FIGS. 6A-6B are a detailed printing diagram corresponding to Example 1 including individual drop locations or voxels.
Figure 6B:
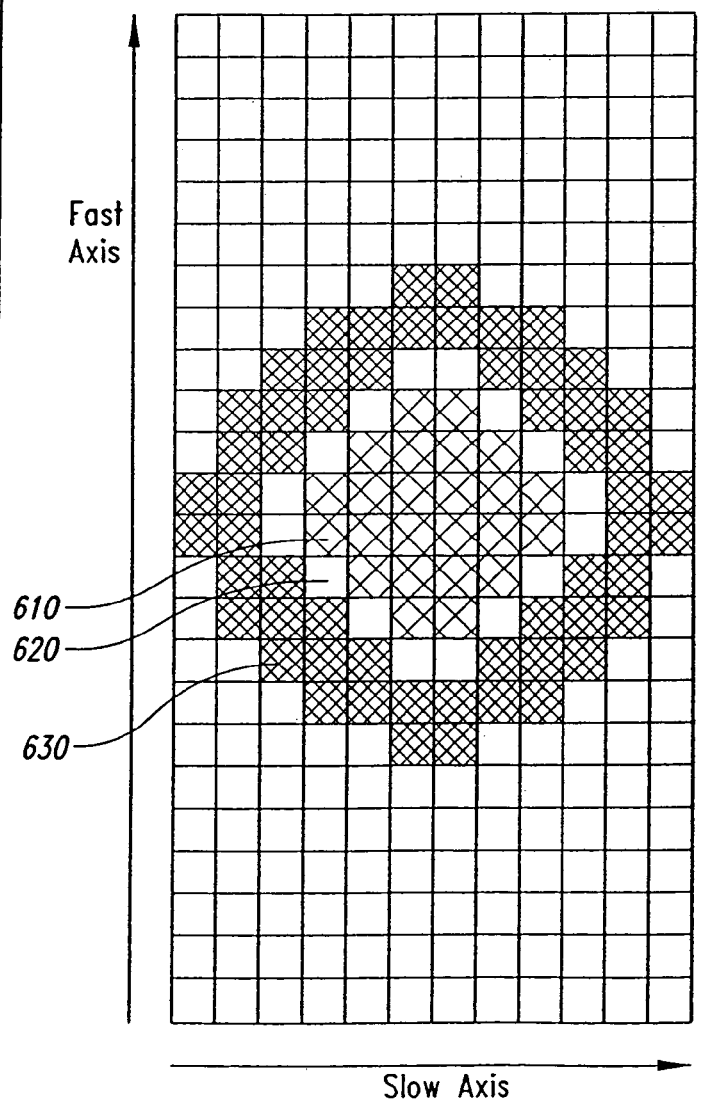
Figure 7A:
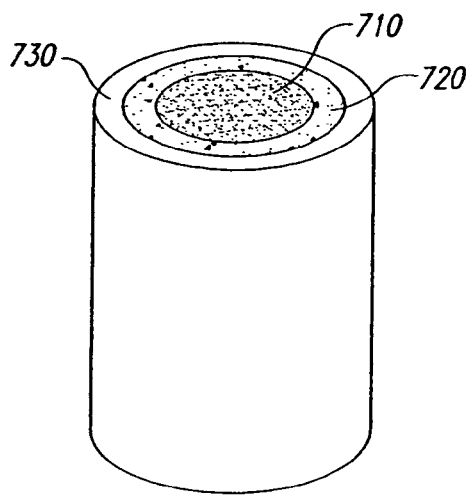
FIGS. 7A-7E are figures illustrating various pharmaceutical forms corresponding to Example 2 including individual regions for two different drugs.
Figure 7B:
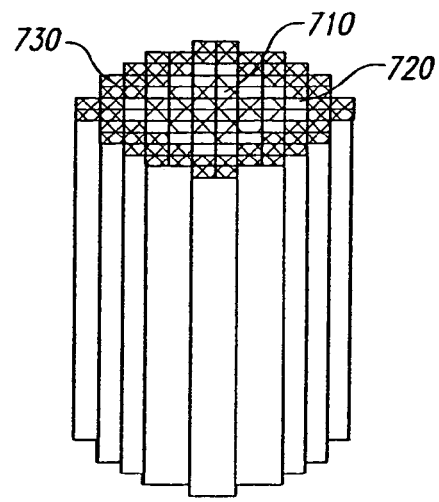
Figure 7C:
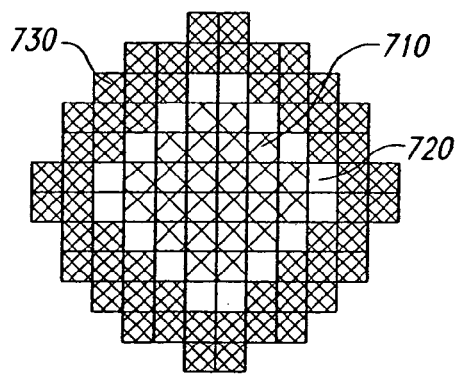
Figure 7D:
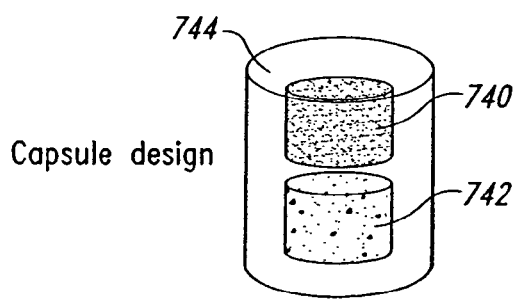
Figure 7E:
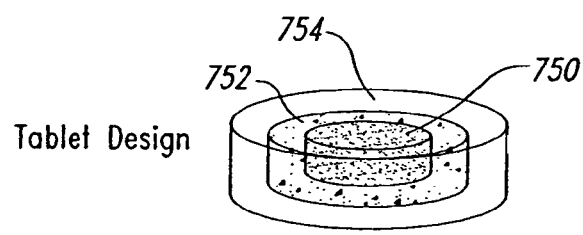

Typical dimensions of tablets 600, shown in FIG. 6A, were 4.8 mm diameter and 12.1 mm long, so as to be able to fit inside a #3 capsule. Printing parameters such as number of voxels (unit cells) in various directions are shown in FIG. 6B. The dimension of a voxel corresponds somewhat to the dimension of a drop and also is influenced by the degree of saturation (filling of void spaces by liquid) desired. For the manufacturing pattern shown here, a typical unit spacing in the horizontal direction is 10 microns. The shell region 630 was fabricated with a binder (dispensed liquid) (shell binder) which was a drug-free solution containing PVP (polyvinyl pyrrolidone) and Tween 20 (polyethylene sorbitan-monolaurate, Sigma Chemical Co., St. Louis, Mo.) which provided appropriate viscosity and surface tension of the liquid. A colorant, FD&C Red No. 40, was also added. The binding of the exterior surfaces (bottom, top and walls) was achieved with this liquid.

FIG. 6B illustrates an important feature of the product design. A buffer region 620 between the core region 610 and the shell region 630, as has already been discussed. The buffer region 620 is occupied by powder which is not printed upon by either the core binder or the shell binder. This provides space into which the core (drug-containing) binder can bleed if needed, without actually reaching the shell. This improves the degree of isolation of the toxic or potent substance from the outside world. In the printing pattern shown here, the dimension of the buffer region 620 in the horizontal direction is one voxel or drop spacing distance or one spatial increment in the slow axis direction. In the vertical direction, similar isolation was provided by printing the bottom surface, and then leaving two or three powder layers with no printing by the core binder, before beginning to print the core binder. In this case the thickness of a powder layer was 400 microns. Because of gravity, bleeding vertically downward (to a previously deposited powder layer) is more serious than is bleeding vertically upward (to a subsequently deposited powder layer). Accordingly, at the top of the printed dosage form, it is possible to similarly leave one or more layers of powder with no core binder printed onto them, but the importance or the required thickness is not so great as it is on the bottom.

Various combinations of excipient types, HPMC (hydroxypropylmethyl cellulose) content and the microstructure of the dosage form matrix were produced by alteration of the fabrication parameters. These various combinations resulted in various different drug release rates. Drug release rates were determined by a USP basket method using 0.1N HCl with or without the presence of surfactant, e.g., sodium lauryl sulfate. A typical drug release duration of a non-encased oral dosage form would be 10 minutes. However, slower initial release rate would be preferable because the irritation by the active to stomach will be minimized. It was found that the drug release duration could be prolonged from 10 minutes to two hours or longer by varying the excipient types. Drug release could be further retarded by increasing HPMC level, e.g., approximately 40% of drug was released at one hour when HPMC content was increased to 50%. The presence of the shell can also have effects on the drug release rate, depending on the shell's thickness, composition, etc., although in this case it was not intended that the shell have significant effect on the release profile.

The packaging of this ODF was such that after manufacture of the dosage form, it was intended that the ODF would be encapsulated with hard shell capsules. Capsules typically come in two halves which slide together forming a close fit. They are typically made of a gelatinous material which dissolves rather quickly in the fluids of the gastrointestinal tract. The dimensions of the dosage form, being 12.1 mm long and 4.8 mm in diameter, lend themselves to fitting inside a #3 capsule.

Example 2

Other drugs of interest are thyroid hormones, triiodothyronine (T3) (molecular weight=650.98 g/mole) and tetraiodothyroxine (T4) (molecular weight=776.87 g/mole). These are hormones which are even more potent per unit mass than the previously described anti-cancer drug. Similar to anti-cancer drugs, hormones have the concern of unwanted personnel exposure to the actives during processing and hence require isolation from personnel who manufacture and handle the product. This example illustrates a different category of drug, namely hormones. For certain therapeutic purposes, these two hormones would need to be included in a single oral dosage form. Thus, this example also illustrates an extra detail of manufacturing beyond Example 1, namely the creation of two geometric drug regions instead of just one. In this example the dispensed liquid is a solution rather than a suspension. The desired drug loading in a tablet is a dosage of T4 per tablet in the range of 25 to 200 micrograms, and a dosage of T3 per tablet in the range of 1.5 to 12 micrograms.

FIGS. 7A-7E illustrate various pharmaceutical forms. Two different shapes are shown here, FIGS. 7D and 7E, one which is appropriate for later insertion inside capsules, and one which is appropriate for tablets without the need of encapsulation. In the capsule geometry, the length is the longest dimension of the dosage form, and so the preferred geometric arrangement of the two individual drug regions is for them to be stacked on top of each other and both enclosed inside a pharmacologically inert shell. For the tablet geometry, the diameter is the largest dimension of the dosage form, and again all the active would have to be surrounded by an inert shell, but it might be preferable to locate one drug region concentrically inside the other drug region, with both of them further being surrounded by the pharmacologically inert shell.

Dispensing of the drug in liquid form would be by techniques similar to those in Example 1, except that for these particular drugs it would probably not be necessary to use a suspension because the combination of the solubility of the drug and the required dosage is such that the needed dosage can be dissolved in the binder liquid.

In the examples presented herein, the example shapes were some form of prism, for example, a cylinder or a rectangular parallelepiped, and therefore all shapes had a flat bottom and a flat top and some shape of sides which filled in the rest of the closed boundary. However, it can well be appreciated that one strength of 3DP in general is its ability to produce complex shapes. Thus, there is no need to limit dosage form shape to shapes having a flat top and bottom. 3DP would be perfectly capable of printing a dosage form which is spherical, or ellipsoidal, or cylindrical with curved top and bottom, or other shape.

The present invention has been discussed in terms of drops of liquid being dispensed. However, it should be understood that in some situations, liquid may be dispensed in ways which are not exactly discrete drops. For example, liquid may be dispensed as a series of lumps of fluid which are connected to each other by narrow strings of liquid. Liquid may even be dispensed as streams which are simply turned on and off or even are physically interrupted by masks. All of these are covered by the present invention. The dispensed liquid may be an aqueous (water-based) liquid as previously disclosed, but it could also be in general any liquid formulation including water, ethanol, other alcohols, chloroform, other halogenated hydrocarbons, acetone, etc., and combinations thereof as appropriate.

The present invention has been discussed in terms of 3DP, which is a prime candidate for manufacturing. However, 3DP is only one of a number of technologies known collectively as solid free-form fabrication (SFF). Other members of this family could also be used.

The ODF can also be further enclosed by a capsule if desired for ease of administering to patients or for appearance or marketing purpose. The capsule could contain either one or a plurality of ODF's manufactured as described herein. A further embodiment could include a coating for purposes of taste, aesthetic appearance or reduced friability.

The invention has been described with respect to toxic anti-cancer drugs and potent hormones, but it could similarly be used with any other toxic or potent compounds with toxicity or potency hazard concerns, such as other anti-cancer drugs, other hormones, steroids, or narcotics.

In Example 1, the shell was not intended to perform any function as far as determining the release rate of the drug. It was made of a substance which would dissolve fairly quickly after being swallowed. However, in other applications it might be useful to design the composition and dimensions of the shell so as to cause the shell to influence the release profile in a desired way, as is known in the art, for example, as described in WO98/3673941.

The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other pharmaceutical forms, possibly even to implantable drug delivery devices, not only to the exemplary oral dosage forms described above.

The various embodiments described above can be combined to provide further embodiments. All of the above patents and applications are incorporated by reference. Aspects of the invention can be modified, if necessary, to employ the process, apparatuses and concepts of the various patents and applications described above to provide yet further embodiments of the invention.

These and other changes can be made to the invention in light of the above detailed description. In general, in the following claims, the terms used should not be construed to limit the invention to the specific embodiments disclosed in the specification and the claims, but should be construed to include all pharmaceuticals that operate under the claims to provide a method for containing a hazardous core. Accordingly, the invention is not limited by the disclosure, but instead the scope of the invention is to be determined entirely by the following claims.

We claim:

1. A three-dimensional printing method of manufacturing a pharmaceutical delivery device comprising: a three-dimensionally printed core region comprising at least one pharmaceutical active printed onto and bound to a solid bulk material; a three-dimensionally printed shell region encapsulating the core region and comprising bound solid bulk material; and a transitional region consisting essentially of unbound or partially bound solid bulk material not printed upon, wherein the transitional region is trapped between the core region and the shell region; and the solid bulk material has the same composition in each region; the method comprising:
  a) providing a layer of the solid bulk material;
  b) dispensing a first fluid onto the layer of solid bulk material to form a first end of the shell region, and optionally repeating a) and b);
  c) providing another layer of solid bulk material;
  d) dispensing the first fluid onto selected portions of the layer in c) to form portions of the wall of the shell region and a first end of the transitional region, wherein the transitional region consists essentially of trapped unbound or trapped partially bound powder not printed upon; and optionally repeating c) and d);
  e) providing another layer of solid bulk material;
  f) dispensing a second fluid containing a pharmaceutical active onto predetermined locations of the layer in e) thereby forming one or more portions of the core region surrounded by portions of the transitional region, and dispensing the first fluid onto predetermined locations of the powder layer in e) thereby forming portions of the wall of the shell region; and optionally repeating e) and f), wherein the transitional region consists essentially of trapped unbound or trapped partially bound powder not printed upon;
  g) providing another layer of solid bulk material;
  h) dispensing the first fluid onto selected portions of the layer in g) to form portions of the wall of the shell region and a second end of the transitional region; and optionally repeating g) and h), wherein the transitional region consists essentially of trapped unbound or trapped partially bound powder not printed upon;
  i) providing a layer of the solid bulk material;
  j) dispensing the first fluid onto the layer of solid bulk material to form a second end of the shell region, and optionally repeating i) and j); thereby forming the three-dimensionally printed dosage form.

2. A method of manufacturing a three-dimensionally printed dosage form comprising a toxic or potent core region encapsulated within a trapped transitional region and a shell region surrounding the transitional region, wherein the transitional region consists essentially of trapped unbound or trapped partially bound powder not printed upon, the method comprising:
  dispensing a first binder fluid which contains neither a toxic or potent excipient onto one or more layers of bulk material to form an end of a shell region;
  providing one or more subsequent layers of bulk material and dispensing the first binder fluid thereon to form an end of a transitional region and a perimeter of shell region, wherein the transitional region consists essentially of trapped unbound or trapped partially bound powder not printed upon;
  providing one or more subsequent layers of bulk material and dispensing thereon: a) on one or more predetermined locations, a second binder fluid containing a toxic or potent pharmaceutical active to form a core region; and b) the first binder fluid to form a perimeter of shell region and a transitional region between the core region and shell region, wherein the transitional region consists essentially of trapped unbound or trapped partially bound powder not printed upon;
  providing one or more subsequent layers of bulk material and dispensing the first binder fluid thereon to form another end of transitional region and a perimeter of shell region, wherein the transitional region consists essentially of trapped unbound or trapped partially bound powder not printed upon; and
  providing one or more subsequent layers of bulk material and dispensing thereon the first binder fluid thereby forming another end of shell region.

3. The method of claim 1 or 2, wherein the first or the second liquid further include a binding agent.

4. The method of claim 1 or 2, wherein the pharmaceutical active is a anti-cancer drug, a steroid, a hormone, a narcotic, or another compound having high toxicity or potency.

5. The method of claim 4, wherein the pharmaceutical active is camptothecin or 9-nitrocamptothecin or other derivatives of camptothecin or triiodothyronine or tetraiodothyroxine.

6. The method of claim 1 or 2, wherein the second liquid contains the pharmaceutical active in solution.

7. The method of claim 1 or 2, wherein the second liquid contains the pharmaceutical active as solid particles suspended therein.

8. The method of claim 1, wherein e) and f) are repeated.

9. The method of claim 8, wherein a) and b), c) and d), and/or g) and h) are repeated.

10. The method of claim 1 or 2, wherein the bulk material comprises one or more pharmaceutical excipients.

11. The method of claim 10, wherein the bulk material further comprises a binder.

12. The method of claim 10, wherein the bulk material further comprises a gelation agent.

13. The method of claim 12, wherein the gelation agent comprises a hydrophilic polymer.

14. The method of claim 13, wherein the hydrophilic polymer is selected from the group consisting of hydroxypropyl methylcellulose, polyvinyl alcohol, polyethylene glycol, polyethylene oxide, carbopol, hydrophilic silica gel, xanthan gum, gellan gum, locust bean gum, acrylic acid polymer, gelatin, sodium carboxymethyl cellulose, methylcellulose, guar gum, sodium alginate, polyethylene-polypropylene copolymer, corn starch, polyvinyl pyrrolidone, and polyoxyethylene alkyl ether.

15. The method of claim 10, wherein the shell region comprises a substance that controls the release of pharmaceutical active from the dosage form.

16. The method of claim 10 further comprising a capsule that completely surrounds the shell.

17. The method of claim 10, wherein the shell region further comprises adhesive or plasticizer.

18. The method of claim 10, wherein the bulk material comprises solid particles of an adhesive.

19. The method of claim 10, wherein the core region further comprises a steric hindrant, suspending agent or both.

20. The method of claim 10, wherein the dosage form provides a delayed release of pharmaceutical active.

21. The method of claim 1 or 2, wherein the transitional region comprises multiple regions of unbound or partially bound powder, which has not been printed upon, surrounding the core region.

22. The method of claim 1 or 2, wherein adjacent layers of the shell region are bound to each other.

23. The method of claim 10, wherein the shell region further comprises a non-toxic pharmaceutical active.

24. The method of claim 23, wherein the non-toxic pharmaceutical active is complementary in action to the pharmaceutical active in the core region.

25. The method of claim 10, wherein the shell region comprises an anti-emetic drug, taste-masking active, sugar, or additive to increase the physical integrity and reduce friability of the dosage form.

26. The method of claim 10, wherein the second fluid further comprises a second toxic or potent pharmaceutical active.

27. The method of claim 10, wherein the one or more predetermined locations in one layer is different than the one or more predetermined locations in another layer.

* * * * *